US011923054B2

(12) United States Patent
Madan et al.

(10) Patent No.: US 11,923,054 B2
(45) Date of Patent: Mar. 5, 2024

(54) AI PLATFORM FOR PROCESSING SPEECH AND VIDEO INFORMATION COLLECTED DURING A MEDICAL PROCEDURE

(71) Applicant: UTECH PRODUCTS, INC., Schenectady, NY (US)

(72) Inventors: Rakesh Madan, Schenectady, NY (US); Zohair Hussain, Schenectady, NY (US); Manish K. Madan, Pittsford, NY (US)

(73) Assignee: UTECH PRODUCTS, INC., Schenectady, NY (US)

( * ) Notice: Subject to any disclaimer, the term of this patent is extended or adjusted under 35 U.S.C. 154(b) by 0 days.

(21) Appl. No.: 17/867,778

(22) Filed: Jul. 19, 2022

(65) Prior Publication Data
US 2023/0026050 A1 Jan. 26, 2023

Related U.S. Application Data

(60) Provisional application No. 63/224,001, filed on Jul. 21, 2021.

(51) Int. Cl.
*G16H 15/00* (2018.01)
*G16H 10/60* (2018.01)
(Continued)

(52) U.S. Cl.
CPC .......... *G16H 15/00* (2018.01); *G16H 10/60* (2018.01); *G16H 30/20* (2018.01); *G16H 30/40* (2018.01); *G16H 50/20* (2018.01)

(58) Field of Classification Search
CPC ........ G16H 15/00; G16H 10/60; G16H 30/20; G16H 50/20; G16H 30/40
See application file for complete search history.

(56) References Cited

U.S. PATENT DOCUMENTS 10,839,164 B1\* 11/2020 Shorter ................ G06N 3/043
11,315,668 B2\* 4/2022 Castine ................ G16H 50/30
(Continued)

FOREIGN PATENT DOCUMENTS

CN 111048170 B 5/2021

OTHER PUBLICATIONS

Venkatesh, Vignesh; "Accelerating Information Retrieval using Natural Language Processing"; International Journal of Computer Science Trends and Technology; vol. 6; No. 3; Jun. 1, 2018; pp. 117-132; <http://www.ijcstjournal.org/volume-6/issue-3/IJCST-V6I3P19.pdf>.

(Continued)

*Primary Examiner* — Jay M. Patel
(74) *Attorney, Agent, or Firm* — Hoffman Warnick LLC

(57) ABSTRACT

An AI based platform for processing information collected during a medical procedure. A method includes capturing images and speech during a medical procedure; processing the images using a trained classifier to identify image-based quality-of-care indicators (QIs); converting the speech into text; parsing the text into sentences; performing a search and replace on predefined text patterns in the sentences; identifying text-based QIs in the sentences; classifying sentences into sentence types using a trained model; updating sentences by integrating the image-based QIs with text-based QIs; and outputting structured data that includes sentences organized by sentence type.

19 Claims, 18 Drawing Sheets

(51) Int. Cl.
*G16H 30/20* (2018.01)
*G16H 30/40* (2018.01)
*G16H 50/20* (2018.01)

(56) References Cited

U.S. PATENT DOCUMENTS

| | | | |
|---|---|---|---|
| 2003/0105638 A1* | 6/2003 | Taira | G06F 40/56 |
| | | | 704/275 |
| 2018/0279943 A1* | 10/2018 | Budman | A61B 5/445 |
| 2019/0057760 A1* | 2/2019 | Schwartz | G06N 3/0445 |
| 2019/0114304 A1* | 4/2019 | Oliveira | G06F 16/285 |
| 2020/0237452 A1* | 7/2020 | Wolf | G06F 3/048 |
| 2020/0334416 A1 | 10/2020 | Vianu et al. | |
| 2020/0411150 A1* | 12/2020 | Saalbach | G06N 20/00 |
| 2021/0216822 A1 | 7/2021 | Paik et al. | |
| 2022/0148691 A1* | 5/2022 | Katouzian | G06F 16/137 |

OTHER PUBLICATIONS

International Search Report and Written Opinion dated Oct. 19, 2022 for PCT/US2022/037562 filed Jul. 19, 2022; pp. 12.

\* cited by examiner

Text Components

| text | type | used pattern |
|---|---|---|
| Colonoscopy throug... | -FIN... | (\W\|^)(stoma)(\W\|$) |
| Midazolam 2.5 mg 1... | -ME... | (\W\|^)(medication) (?'VALUE'(.+)(\W\|$)) |
| Midazolam 6 mg | -ME... | (\W\|^)(medication) (?'VALUE'(.+)(\W\|$)) |
| Tortous sigmoid, Re... | -FIN... | (\W\|^)(sigmoid)(\W\|$) |
| Ileocecal valve | -EXT... | (\W\|^)(reached) (?'VALUE'(.+)(\W\|$)) |
| How is the weather... | ? | |
| What are you doing... | ? | |
| The colon appeared... | -FIN... | (\W\|^)(colon)(\W\|$) |
| Internal hemorrhoids | -FIN... | (\W\|^)(hemorrhoid(s\|))(\W\|$) |
| Remainder unremar... | -FIN... | ((from)\|(to))(.+)(cecum) |
| Diverticulosis in sigm... | -FIN... | (\W\|^)(diverticulosis\|diverticulitis\|diverticular\|diverticul... |
| 3 polyps found in an... | -FIN... | ^((?=.*( in ))(?=.*((\W\|^)polyp(s\|)(\W\|$))) |
| Partially removed | -FIN... | (\W\|^)(removed\|retrieved)(\W\|$) |
| Biopsy obtained, res... | -FIN... | (\W\|^)(biops)(.+)( )((obtain)\|(taken)) |

| CPT Code | Interventions | Procedure Name Relation (regex pattern) |
|---|---|---|
| 45381 | India Ink | (\W:^)colon\(.) |
| 91110 | Gastrointestinal tract imaging, Esophagus through ileum ... | (Capsule Endoscopy) |
| 91111 | Gastrointestinal tract imaging, Esophagus with interpreta... | (Capsule Endoscopy) |
| 44388 | through stoma | (\W:^)colon\(.) |
| 44389 | stoma, biopsy | (\W:^)colon\(.) |
| 44390 | stoma with foreign body removal | (\W:^)colon\(.) |
| 44391 | stoma continuous bleeding | (\W:^)colon\(.) |
| 44392 | through stoma, hot biopsy | (\W:^)colon\(.) |
| 44394 | through stoma, snare | (\W:^)colon\(.) |
| 45378 | diagnostic | (\W:^)colon\(.) |
| 45379 | foreign body removal | (\W:^)colon\(.) |
| 45380 | cold biopsy | (\W:^)colon\(.) |
| 45381 | submucosal injection | (\W:^)colon\(.) |
| 45382 | control bleeding | (\W:^)colon\(.) |
| 45384 | hot biopsy | (\W:^)colon\(.) |
| 45385 | snare | (\W:^)colon\(.) |
| 45386 | dilation stricture | (\W:^)colon\(.) |
| G0105 | screening, high risk | (\W:^)colon\(.) |
| G0121 | screening, average risk | (\W:^)colon\(.) |
| 43211 | esophagoscopy, flexible, transoral; with endoscopic muco... | (EGD)|(Esophagogastroduodenoscopy) |

AI PLATFORM FOR PROCESSING SPEECH AND VIDEO INFORMATION COLLECTED DURING A MEDICAL PROCEDURE

TECHNICAL FIELD

The subject matter of this invention relates to extracting and processing clinical information from unstructured data and image data collected during a procedure.

BACKGROUND

Doctors and other medical professionals (i.e., clinicians) spend large amounts of time documenting information obtained from medical procedures. This process includes dictating information, reviewing dictation, editing reports and letters, entering information into software applications, etc. The end result is that medical professionals have less time to spend on patient care.

SUMMARY

Aspects of the disclosure provide an artificial intelligence (AI) platform for extracting clinical information from speech and image data collecting during a procedure and generating structured information. The resulting information may for example be utilized to generate a report, populate an electronic medical records (EMR) database, provide quality-of-care indicators, etc. The AI platform utilizes a text classifier with natural language processing, pattern recognition, next word prediction and image classification to integrate and generate structured data.

In one aspect, an AI platform for processing information collected during a medical procedure is provided, comprising: an image processing system that processes images captured during the procedure using a trained classifier to identify image-based quality-of-care indicators (QIs); a natural language (NL) processing system that processes captured speech uttered during the procedure and includes: converting the speech into text; parsing the text into sentences; performing a search and replace on predefined text patterns; identifying text-based QIs in the sentences; classifying sentences into sentence types based on a trained model; and updating sentences by integrating the image-based QIs with text-based QIs; and an output module configured to output structured data that includes sentences organized by sentence type and images organized by image-based QIs.

In another aspect, a method for processing information collected during a medical procedure is provided, comprising: capturing images and speech during a medical procedure; processing the images using a trained classifier to identify image-based quality-of-care indicators (QIs); converting the speech into text; parsing the text into sentences; performing a search and replace on predefined text patterns in the sentences; identifying text-based QIs in the sentences; classifying sentences into sentence types using a trained model; updating sentences by integrating the image-based QIs with text-based QIs; and outputting structured data that includes sentences organized by sentence type.

In a further aspect, a system is provided comprising: a camera for collecting image data during a medical procedure; a microphone for collecting speech during the medical procedure; an image processing system that processes image data using a trained classifier to identify image-based quality-of-care indicators (QIs); a natural language (NL) processing system that processes captured speech uttered during the procedure and is configured to: convert the speech into text; parse the text into sentences; perform a search and replace on predefined text patterns; identify text-based QIs in the sentences; classify sentences into sentence types based on a trained model; and update sentences by integrating the image-based QIs with text-based QIs; and an output module configured to output structured data that includes sentences organized by sentence type and images organized by image-based QIs.

Other aspects may include one or more of the following. The system or methods wherein the procedure includes a colonoscopy and the image-based QIs include landmarks involving at least one of: a cecum, a rectum, an ascending colon, a descending colon, and a hemorrhoid; wherein the image-based QIs further include at least one of: polyps detected, polyp size, and histology; wherein performing a search and replace on predefined text patterns includes using regular expressions (regex) to identify patterns; wherein the procedure involves detecting and/or analyzing lesions; wherein identified patterns are replaced with standardized medical expressions; wherein the NL processing system further includes filtering out irrelevant sentences; wherein the NL processing system further includes providing an editor for displaying and editing sentences, wherein the editor includes a next word prediction system; wherein the next word prediction system uses Markov Chain Algorithm and model trained on a database of medical records; wherein the output module is configurable to output a medical report, an Electronic Medical Record (EMR), or a QI registry entry; and/or wherein the output module is configurable to output a medical report with sections organized by sentence type.

BRIEF DESCRIPTION OF THE DRAWINGS

These and other features of this invention will be more readily understood from the following detailed description of the various aspects of the invention taken in conjunction with the accompanying drawings in which:

FIG. 4 shows an illustrative replace list editor of the AI data integration tool according to embodiments.

FIG. 5 shows an illustrative expression replacement manager according to embodiments.

FIG. 6 shows a classification interface according to embodiments.

FIGS. 7-9 show a quality-of-care indicators manager interface according to embodiments.

FIG. 10 shows an intervention/CPT code manager interface according to embodiments.

FIG. 16 depicts a summary view of the AI data integration tool according to embodiments.

Figure 1:
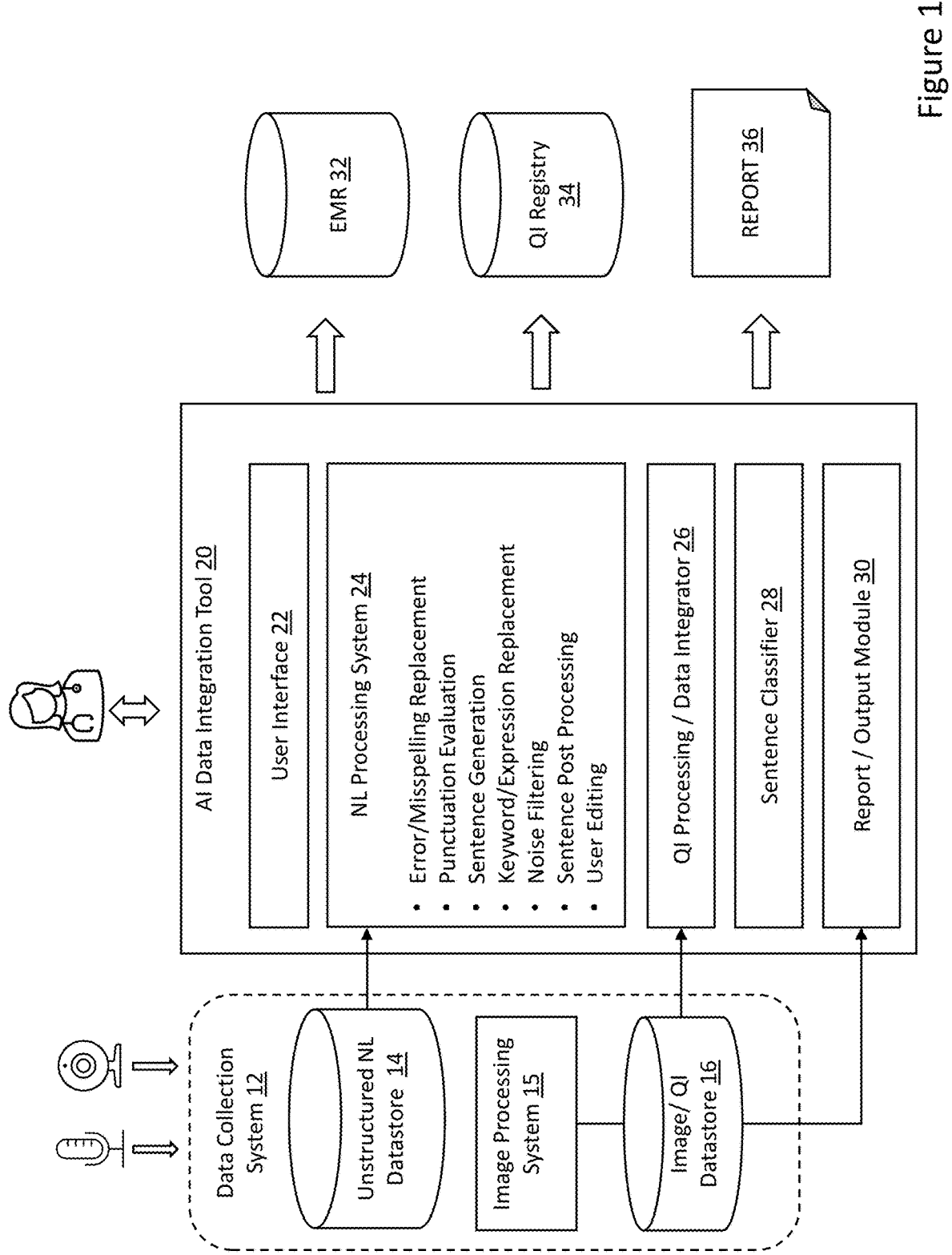
FIG. 1 shows an artificial intelligence (AI) platform according to embodiments.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION

Embodiments of the present disclosure describe a platform for collecting and processing information generated during a medical procedure, such a gastroenterology procedure. Although illustrative embodiments include a colonoscopy procedure, it is understood that the solution could be applied to any clinical procedure, including those that analyze and detect lesions. The platform provides a technical solution to address the time-consuming process of manually managing, analyzing, integrating and reporting information resulting from procedures. In certain aspects, an AI platform is provided that will automate and streamline information processing of mixed media clinical data collected during a procedure, including audio (e.g., natural language "NL" speech uttered by a doctor during a procedure) and video (e.g., streamed images captured by a camera during a procedure). The platform outputs relevant clinical data in a structured format and eliminates manual actions, such as point and click workflows from clinical application settings. The platform uses various techniques to identify relevant information and remove unnecessary data, e.g., unwanted sentences uttered during a procedure. The resulting structured clinical data can for example be used for clinical report generation, statistical analysis, registry reporting, etc.

FIG. 1 depicts an illustrative AI platform that generally includes two components, a data collection system 12 and a data integration tool 20. Data collection system 12 is configured to collect data during a clinical procedure, including audio collected from a microphone and video collected from a camera (e.g., on a scope). Audio data generally includes natural language (NL) spoken by one or more of the clinicians or doctors performing the procedure and is stored in an unstructured NL datastore 14 (either as an audio recording or converted text). In one embodiment, image data is collected and processed in real time by image processing system 15, which may for example utilize AI to analyze images to generate information such as landmarks, polyp size, lesion characteristics, location or count information, etc., from images captured or streamed during a procedure such as a colonoscopy. The generated information may include what is generally referred to herein as quality-of-care indicators (QIs). The resulting image data and QIs are stored in an image/QI datastore 16.

After the procedure is completed, the clinician is able to interact with the data integration tool 20 via a user interface 22. Data integration tool 20 includes an NL processing system 24 configured to process NL stored in the unstructured NL datastore 14 and generate structured clinical data. Illustrative processes, which are described in further detail herein, include error/misspelling replacement, punctuation evaluation, sentence generation, keyword/expression replacement, noise filtering, sentence post processing, and user editing.

Data integration tool 20 also includes a QI processing/ data integrator 26 that integrates image-based QI data with text-based QI data to provide structured clinical data. In one illustrative embodiment, the structure clinical data includes various classifications or types, such as: Procedure Performed, Extent of Exam, Medications, Findings, Diagnosis, Limitations of Exam, ICD, CPT codes, QIs and data element for the registries (e.g., GIQuIC). A sentence classifier 28 is provided to classify sentences that make up the structured clinical data into appropriate categories or sentence types, e.g., procedure performed, findings, diagnosis, recommendations, etc. Report/Output module 30 is configured to generate a report 36 or otherwise output information in a structured format for another system, such as an electronic medical record (EMR) system 32, a QI registry 34, etc.

Figure 2:
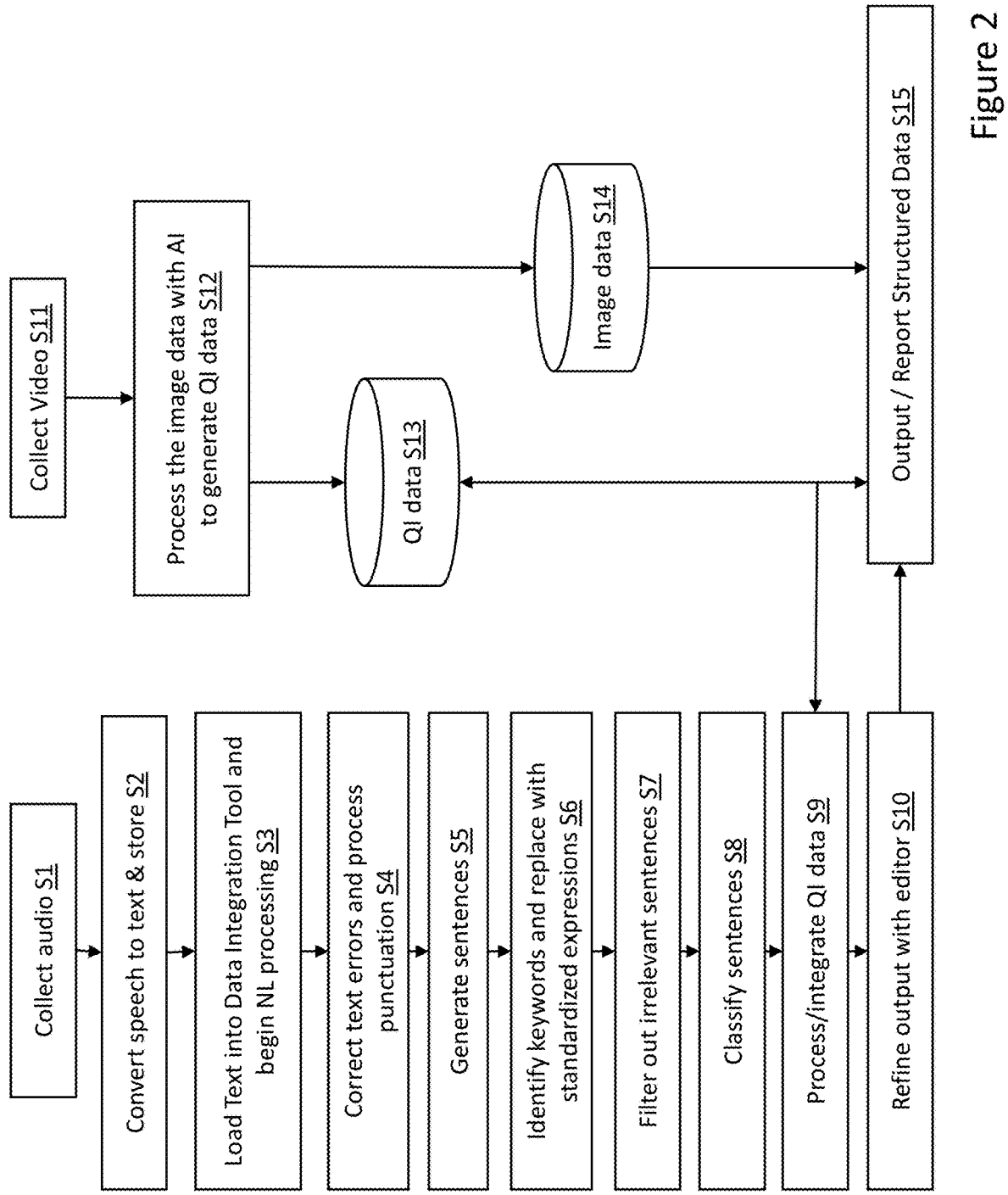
FIG. 2 shows a process performed by the AI platform according to embodiments.
Figure 3:
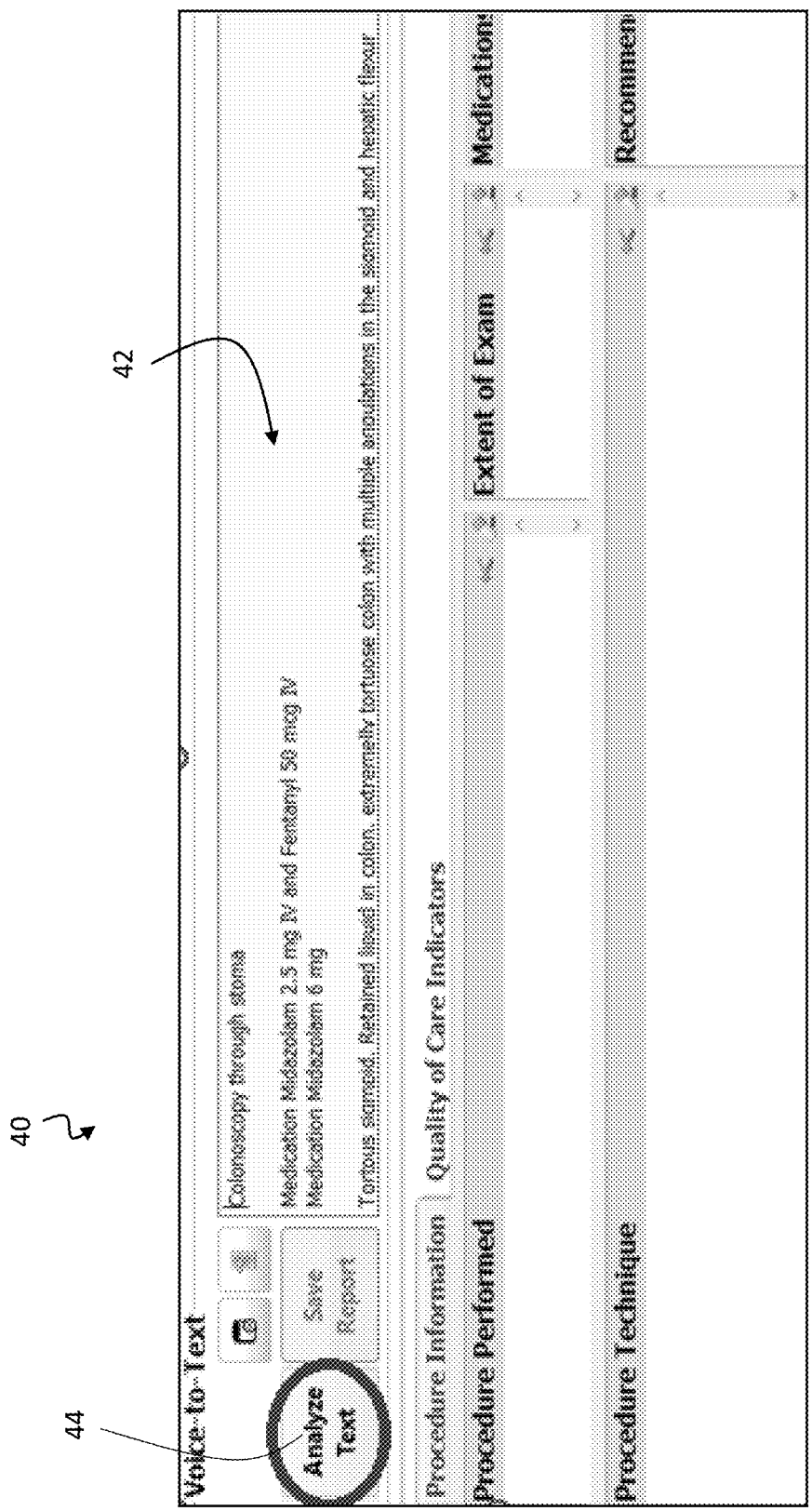
FIG. 3 shows an illustrative interface of an AI data integration tool according to embodiments.

FIG. 2 depicts a flow chart of an illustrative process using the platform of FIG. 1. As shown, the flow includes two paths, collect audio at S1 and collect video at S11. In the collect audio path S1, speech is converted to text and the NL is stored in the NL datastore 14 at S2. The conversion may be implemented by the data collection system 12, the NL processing system 24, or some other system. In the case where the conversion is done by the data collection system 12, the text is loaded into the data integration tool 20 and NL processing begins. FIG. 3 depicts an illustrative interface view 40 of tool 20. In this example, the NL appears in a window 42, and the user begins the process by selecting the analyze text button 44. Once the analysis is launched, unstructured NL text (i.e., speech) is processed by a system that provides replacement list processing and sentence generation.

In one illustrative embodiment, the text is processed using regular expression (regex) techniques. Regular expressions are a series or sequence of characters that can replace a set of patterns in a text dataset. Regular expressions can be used for string related functions such as searching a string or replacing a string. Types of regular expressions may for example include: digits (e.g., 1/2/100); alphabets (e.g., a/v/ t); any character (e.g., +/?/<); and set of digits. Illustrative regex functions include: search to find a specific pattern in a string; match to find the very first occurrence of a pattern in a string; find all to find all the patterns in a given string; split to split the text into the given regular expression; and sub to search and replace in string.

Returning to S4 in FIG. 2, a first step of processing text includes correcting text errors and processing punctuation. Namely, the unstructured dictated text is searched with a replacement list that will replace identified strings with replacement strings. The replacement process performs this according to pre-defined rules defined in a replacement table. In step S4, there are two illustrative types of records in the replacement table: "End of Sentence Skip" and "Replace Pattern". Processing punctuation is handled by "End of Sentence Skip" replacement to identify punctuation (e.g., periods) that is not indicative of an end of sentence. This replacement type is used to prevent the sentence generation mechanism from inadvertently forming sentences when a period is located, e.g., periods in words such as "Dr.", "*H. pylori*", "vs.", etc., will have the periods temporarily removed. "End of Sentence Skip" changes are temporarily made, and the periods are returned into the text after all text processing is completed. "Replace Pattern" is used to correct text errors such as incorrectly entered text or misspelled words (e.g., "seaside polyp" will replace to the "sessile polyp").

Figure 4:
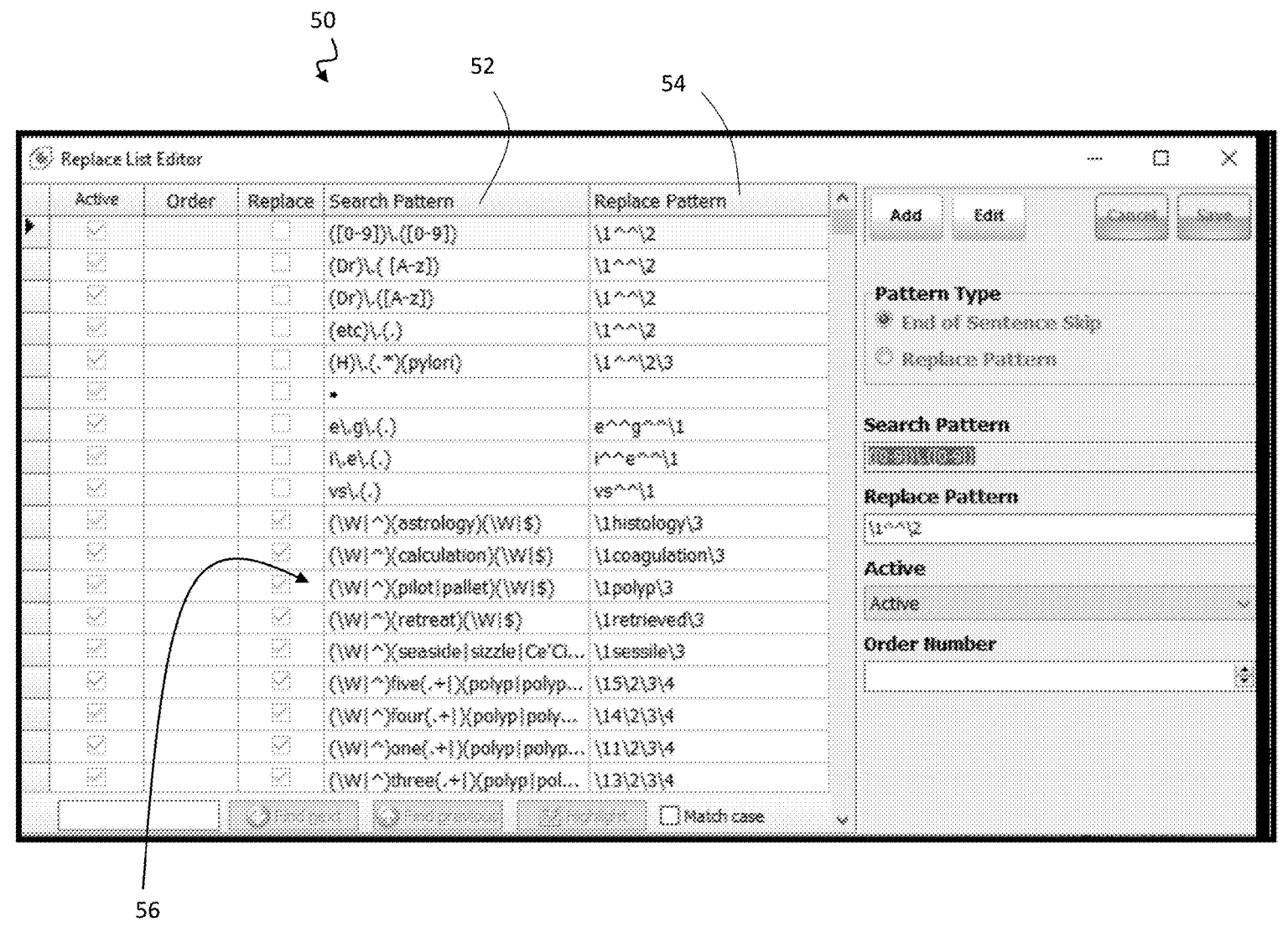

FIG. 4 depicts an example replacement list editor 50 that specifies search and replace patterns using regex. Replacement list editor 50 may for example be populated ahead of time manually by an expert or by an automated learning process. As shown, editor 50 includes a search pattern column 52 and a replace pattern column 54. For example, as shown on row 56, the words "pilot" and "pallet" are replaced with "polyp".

Next, at S5 in FIG. 2, sentences are generated by splitting dictated text into parts (generally referred to herein as "sentences." In one illustrative embodiment, sentences are created based on sentence separators, such as ".", End of line, "!", "?", etc.

Figure 5:
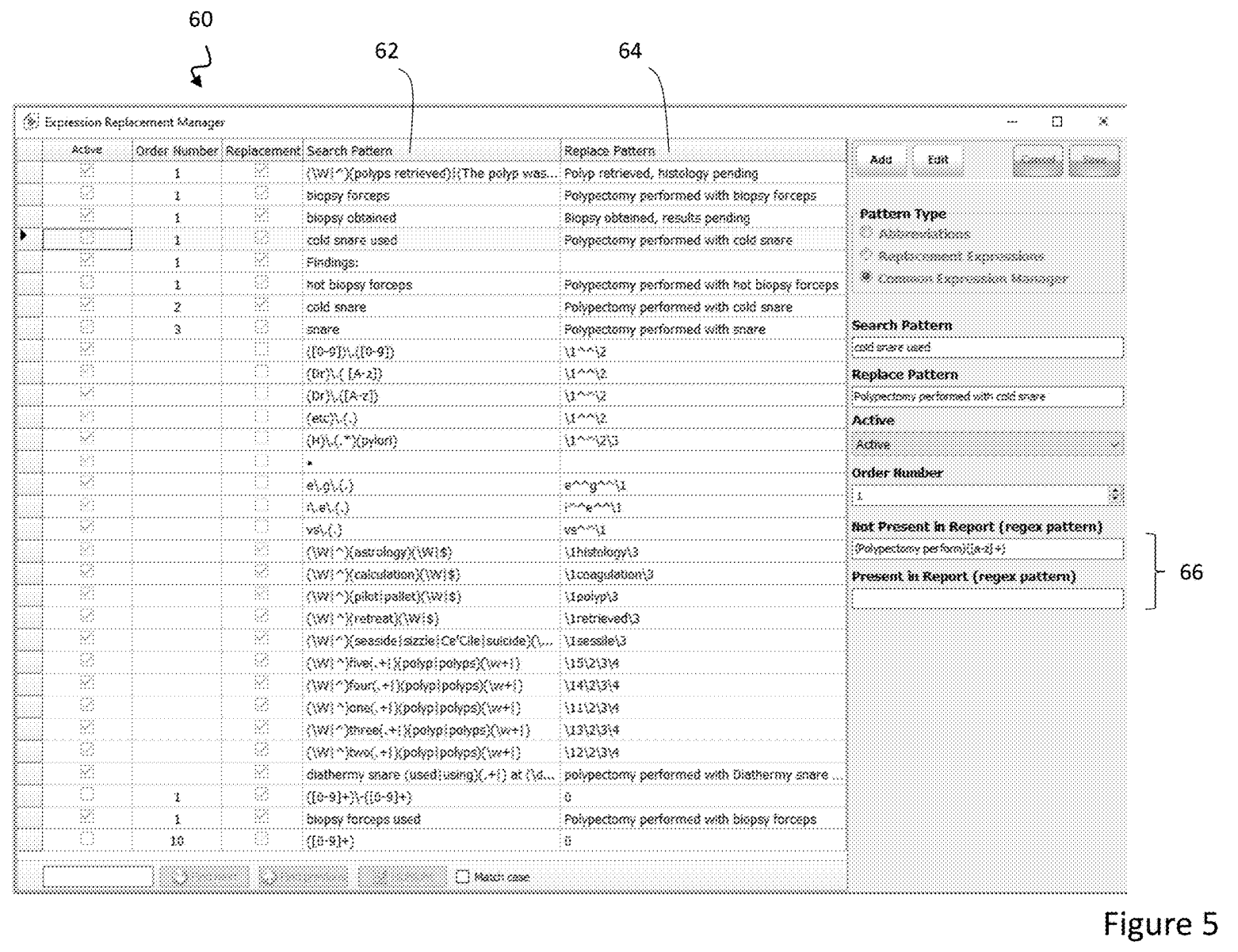

Once the sentences are generated, keywords are identified and replaced with standardized expressions. For example, less formal terms uttered by the doctor to describe something in the unstructured text are replaced with standardized expressions from a medical dictionary. FIG. 5 depicts an illustrative expression replacement manager 60 for handling the process. This replacement process is likewise based on regex patterns in which keywords and phrases in processed sentences are replaced with replace patterns 64. For example, each sentence is searched for a search pattern 62, e.g., based on a complete match. For example, if a user says, "Polypectomy performed" during the dictation, in the final parsed data, it will show as "Polypectomy performed, Histology Pending."

In certain embodiments, if a record is found in the search pattern list 62, the replacement process will further check for other conditions, such as Not Present and Present in Report conditions 66, before performing a replacement. For instance, if the two associated boxes 66 are populated for an identified search pattern 62, two additional conditions must be met to have the identified search pattern replaced with a replace pattern 64. In a first condition, the contents of the first box "Not Present in Report" must not be present anywhere in the text. For example, "Polypectomy performed" must not be present in order for the located text "cold snare used" to be replaced with "Polypectomy performed with a cold snare". In a second condition, if the second box "Present in Report" contains a value, that value must be present in the text. For instance, if the second box included the term "colonoscopy", the second condition will be met if "colonoscopy" is present anywhere in the text. In this embodiment, if both conditions are not met, replacement will not happen. These additional conditions allow the users to customize replacement strategies.

Next, at step S7 in FIG. 2, irrelevant sentences (i.e., noise) are filtered out. Filtering may likewise use regex patterns to identify words indicative of irrelevant sentences, e.g., "weather", "kids", "baseball", etc.

At S8, sentences are classified by a model to determine a sentence type, e.g., which part of the report does it belong to. For example, FIG. 6 shows a table in which sentences 70 are classified as a type 72 based on regex patterns 74 detected in the sentence. Illustrative types include, e.g., FIN (Findings), ME (Medications), EXT (Extent of Exam), etc. Note that the table also shows sentences 76 that were filtered out in the previous step S7. The model (i.e., regex patterns and types) may for example be based on the contents of historical data used to train an AI model.

The sentence can be further evaluated based on the classification, and unwanted words can be removed using regex patterns. For example, for sentences classified in "Extent of Exam," the located text "reached cecum" can be replaced with "cecum" using the expression "(\W|^)(reached) (?'VALUE'(. +|)(\W|$))"="cecum".

Returning again to the collect video step S11 in FIG. 2, video is processed using AI techniques at S12 to determine and store S13 quality-of-care indicator data (QIs). Video image data S14 is likewise stored. Image processing can utilize any technique that analyzes images and outputs image-based QIs, e.g., polyps detected, size, histology, etc. An illustrative technique for sizing and detecting lesions and polyps is described in U.S. Pat. No. 10,957,043, issued on Mar. 23, 2021, which is hereby incorporated by reference.

As QI data can be obtained from both the speech data as well as the image data, the QI data from both is processed and integrated at S9. For example, an image-based QI, "One polyp found in sigmoid colon" could be output by a lesion detection AI module during image processing. A physician might also dictate the text-based QI "Two polyps found in ascending colon," which would be presented in a sentence. Accordingly, the information from both can be integrated together so a final integrated QI finding would be: "Number of polyps=3", and the associated sentence can be updated, e.g., "Three total polyps found—two polyps found in ascending colon, and one in the sigmoid colon."

Figure 7:
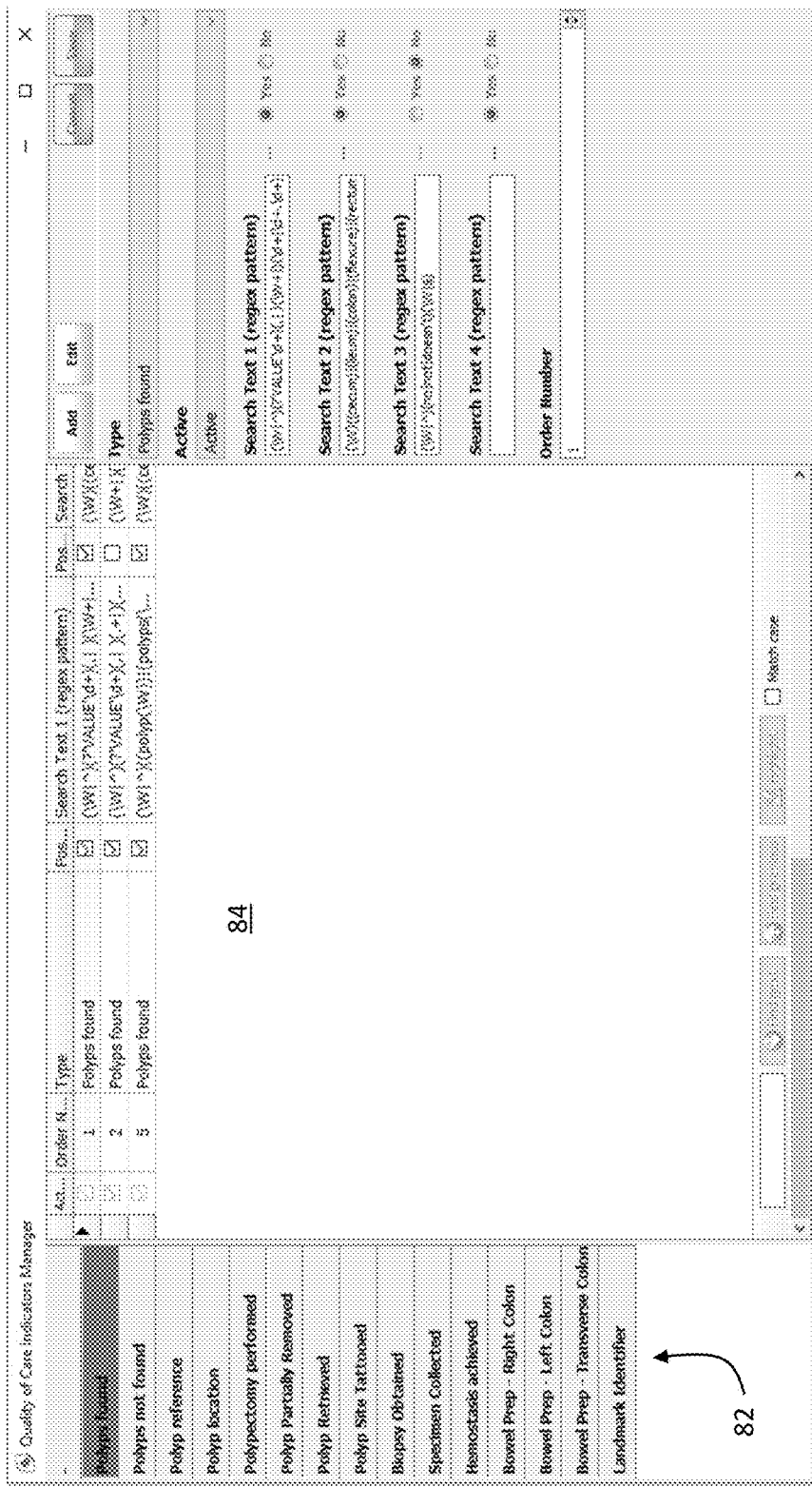
Figure 8:
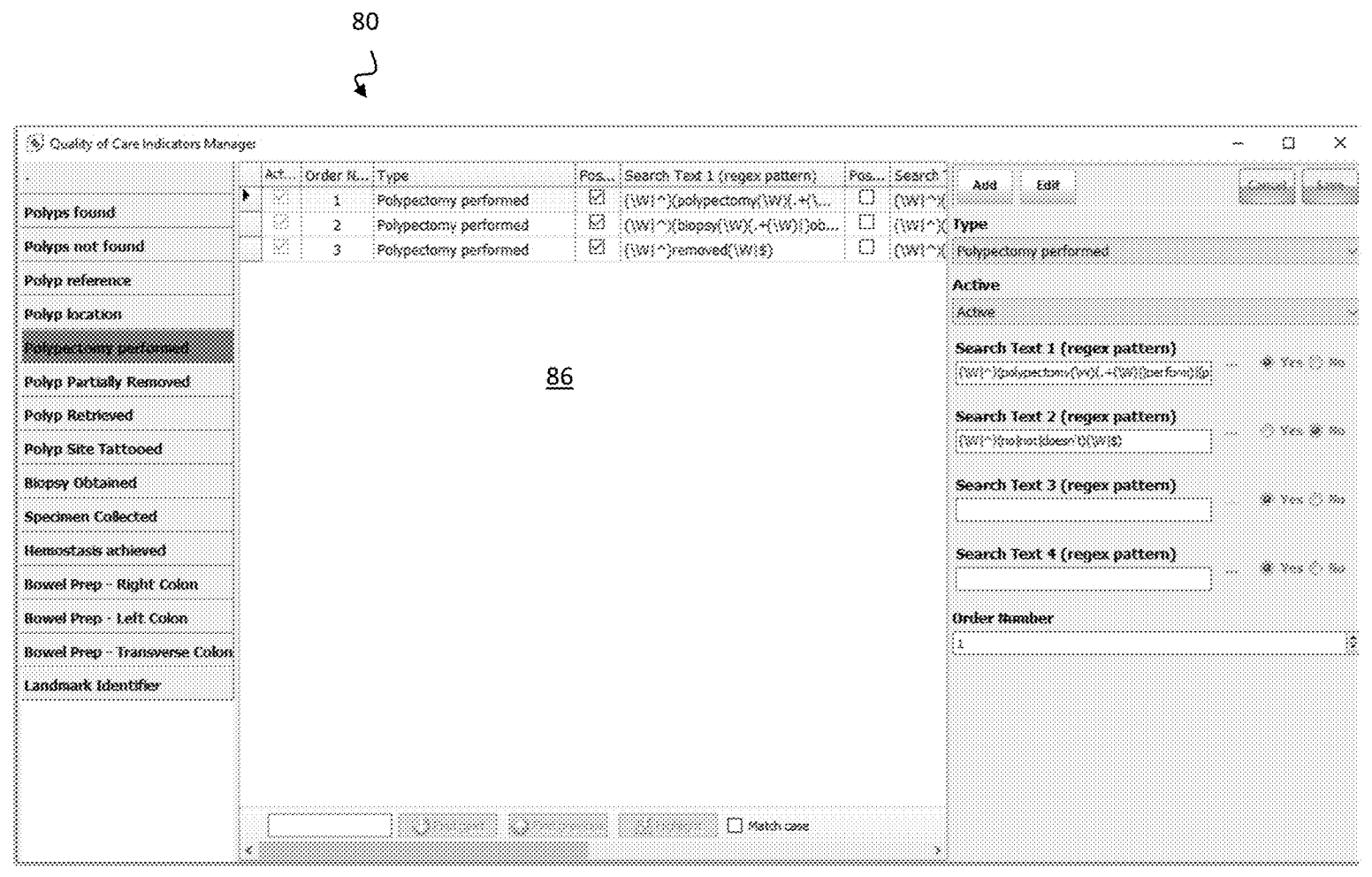
Figure 9:
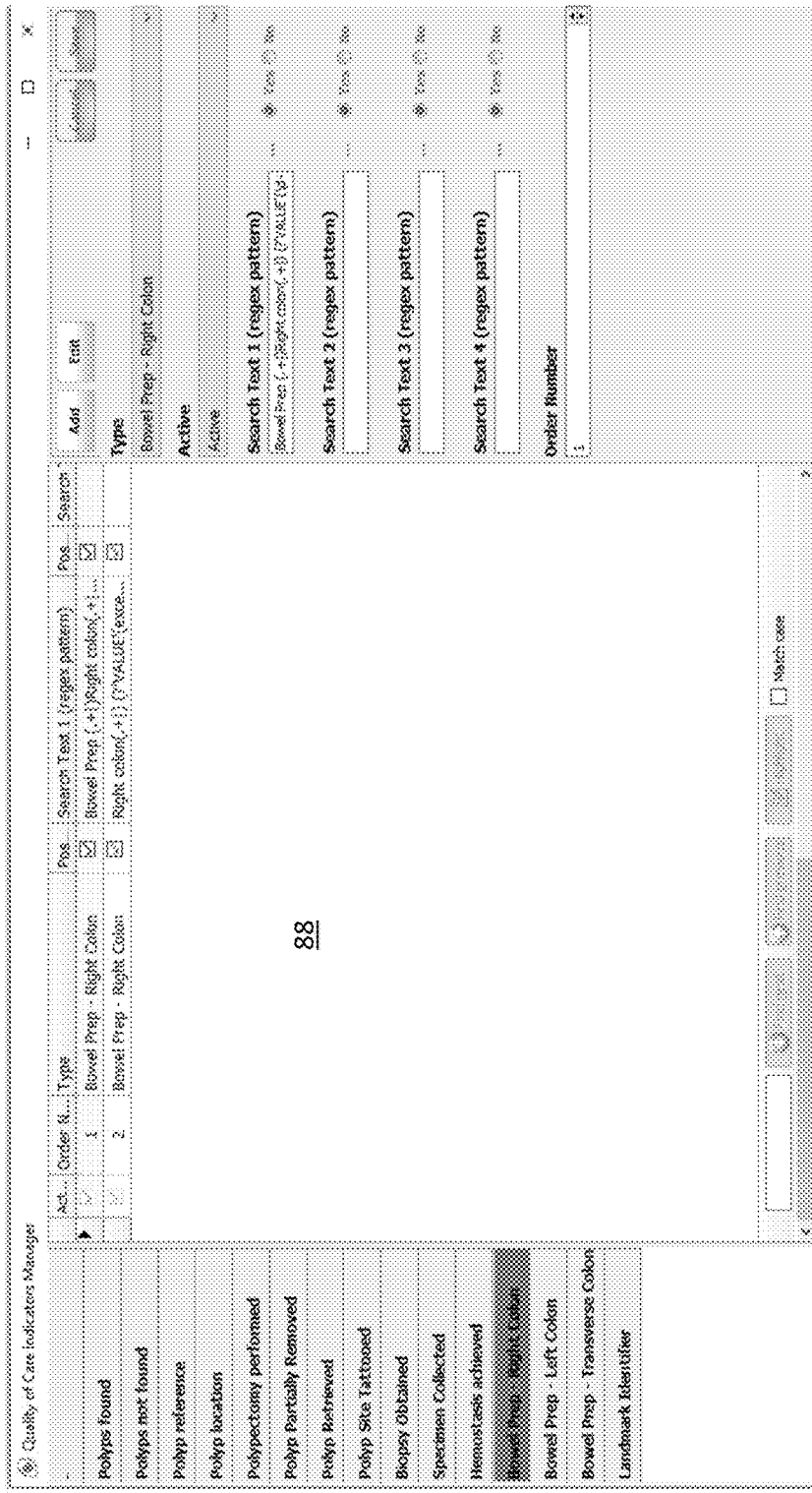

FIGS. 7-9 depicts different views of a quality-of-care indicators (QI) manager 80 for extracting QI information from generated sentences. As shown in FIG. 7, the left-hand column in QI manager 80 provides a list of selectable QI types 82, e.g., Polyps found, Polyps not found, etc. For each QI type 82, there are a set of regex patterns 84 that map to a QI value, e.g., yes/no, a number or count, a location, a value, etc. For example, based on a search for the regex patterns 84 in FIG. 7, a yes or no value is returned indicating whether a polyp was found. Similarly, based on a search for the regex patterns 86 in FIG. 8, a yes or no value is returned indicating whether a polypectomy was performed. In FIG. 9, based on a search for the regex patterns 86, a bowel prep location and value are obtained. Each of the listed QI types in the manager 80 are evaluated as part of the QI data processing in step S9 (FIG. 2) to create a set of structured QI findings.

After the QI values are determined from the QI manager 80, they can be further integrated and updated based on the image-based QI data S13 generated from the image data processing step or based on previously stored data. For example, polyps found value may change from yes to no or no to yes, the number of polyps found value may be increased, if a polypectomy was performed, the total number of polypectomies might be recalculated. The generated sentences can be updated based on the integration process.

FIG. 10 depicts an Intervention/CPT Code Manager 90, which compares each sentence in the text to all CPT code descriptions in the CPTCODES table. Only CPT codes related to the current procedure name are selected. To establish a relationship between CPT codes and procedure names, the INTERVENTIONS table is used. The selected CPT codes may be sorted by relevance rank, and, e.g., the top five CPT codes are presented to the user. The relevance rank may be provided by the SQL server. The top three interventions related to the selected CPT codes are used as procedure performed text.

Once a structured set of sentences are generated, an editor may be utilized at S10 by the user to refine the output. In some embodiments, the editor includes language modeling, i.e., next word prediction which, for a given character, or a sequence of characters, automatically generates the most probable next character or sequence of characters (e.g., words, phrases, etc.). This feature accordingly further reduces the time a clinician is required to interact with the data to complete a report or the like.

Language modeling may utilize a trained model to allow word searching using NLP and deep learning AI. In this case, the input to the model is a sequence of characters, and the model is trained to predict the output using historical information. For example, to predict the next word in the sentence "Polypectomy performed with _____", (1) a recurrent neural network (RNN) neuron receives a command that indicates the start of a sentence, (2) the neuron receives the word "Polypectomy" and then outputs a vector of numbers that feeds back into the neuron to help it "remember" that it received "Polypectomy" (and that it received its first). The same process occurs when it receives "performed" and "with," with the state of the neuron updating upon receiving each word; (3) after receiving "with," the neuron assigns a probability to every word in the clinical findings data vocabulary which is created to complete the sentence. The RNN might assign the word "cold snare" one of the highest probabilities and will choose it to complete the sentence.

Examples of predicting text associated with clinical findings are shown in bold below, e.g., based on highest percentage: 2 mm Flat polyp in the cecum. Polypectomy performed with cold snare. Polyps retrieved. Histology pending. 3 mm sessile polyp in the mid ascending colon. Polypectomy performed with cold snare. Polyp retrieved. Histology pending. 3 mm sessile polyp in the splenic flexure, 50 cm from the anorectal verge. Polypectomy performed with hot biopsy forceps. Polyp retrieved. Histology pending. Internal hemorrhoids.

Figure 11:
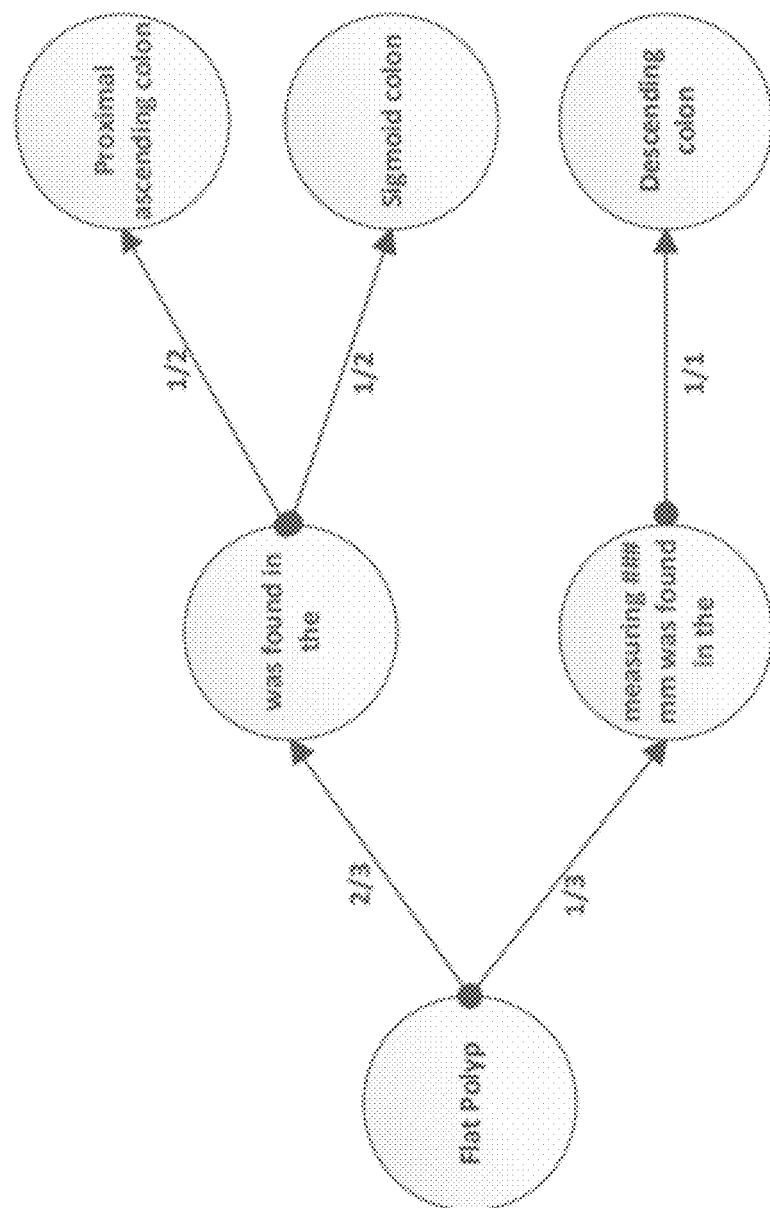
FIG. 11 shows a hierarchy for performing next word prediction according to embodiments.

In a further embodiment, predictive typing may utilize a Markov Chain Algorithm. Examples of predicting text associated with clinical findings are shown in bold below and an associated hierarchy is shown in FIG. 11.

Flat Polyp was found in the proximal ascending colon.
Flat Polyp was found in the Sigmoid colon.
Flat Polyp, measuring ###mm was found in the proximal ascending colon All the unique phrases from above sentences, i.e., "Flat Polyp", "was found in the", "proximal ascending colon", "measuring ###mm was found in the", "Sigmoid colon", and "Descending colon" could form the different states. Representing the above work mathematically as conditional probabilities:

P (was found in the|Flat Polyp)=0.67
P (Measuring ###mm found in the|Flat Polyp)=0.33
P (Proximal ascending colon was found in the)=P (Sigmoid colon was found in the)=0.5
P (Descending colon|Measuring ###mm found in the)=1

The same conditional probabilities can be implemented to single word instead of the phrases.

Sections from an EMR database of procedure records, e.g., Findings, Diagnosis, Indications, Recommendations, etc., may be used to train a predictive model. In this case, text in procedure reports is split into sentences. Duplicate sentences are removed and sentences with uncommon words, e.g., the ones found less than four times in all sentences intended for training are removed to eliminate irrelevant words. In one example, 946,198 unique sentences and 15,942 unique words were collected for training.

Different techniques may be used for word prediction and sentence prediction training. Word prediction training includes building a word hierarchy based on frequency of word usage in the training set. The output may show suggested word options according to that hierarchy. Sentence prediction training includes the following steps:
1. Tokenization
2. Building the state pairs
3. Determining the probability distribution At first, tokenization is performed that breaks down a sentence into words. The second stage consists of forming previous and current state pairs. If a 5th-order Markov model is used, the previous state will consist of one to five words. The words in each sentence are grouped by the number of words with a maximum number of words of 5: one-word groups, two, three, four, and five-word groups. For example, in the sentence "Serrated polyp found in the descending colon," one-word groups include: serrated, polyp, found, in, the, descending, and colon. Two-word groups include: serrated polyp, polyp found, found in, in the, the descending, descending colon, etc. The groups with the same number of words from all sentences are combined into large groups, so, five final word groups are created. Duplicate word groups are removed.

All sentences in the training set (946,198) are analyzed for each word group to identify the next possible word and probability of its appearance. Then a hierarchy of possible words are built for each word group. For a sample sentence above, the "found" is the next possible word for a two-word group "serrated polyp". As a result of training, when a user types in "serrated polyp", the system immediately cycles through the options: "serrated polyp—found—in—the—descending—colon" and comes up with the whole sentence in the suggested options. An illustrative hierarchy is shown in FIG. 11.

Figure 12:
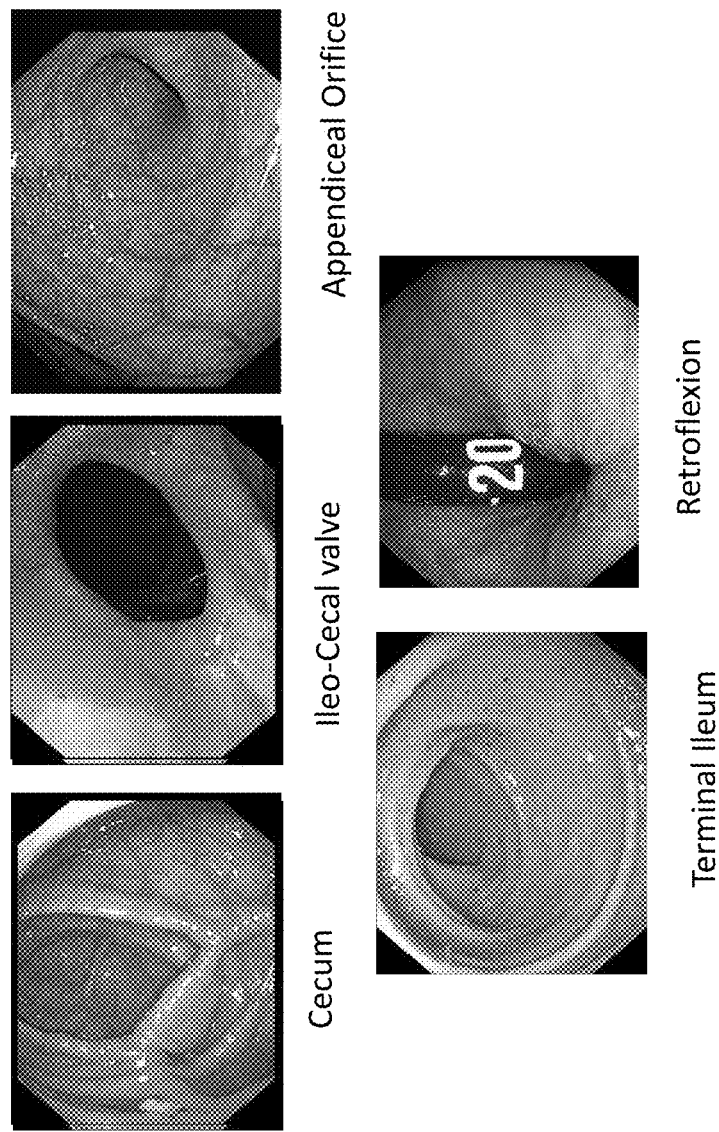
FIG. 12 depicts landmark images according to embodiments.

Referring again to the image processing at S12 in FIG. 2, an image classifier may be deployed as follows. Landmark identification in an endoscopy procedure is vital and one of the essential quality-of-care indicators. FIG. 12 shows examples of various landmarks. The image classifier is trained using deep learning with pictures of all the landmarks. The AI identifies each landmark and timestamps it, which can for example be sent to an EMR system as a quality-of-care indicator. The classifier, e.g., identifies the cecum, rectum, etc., with a timestamp and calculates the cecal intubation time and withdrawal time, important QI measures. The image processing can be used to analyze digitized image frames captured during colonoscopy procedure. Information like insertion time, withdrawal time, images at the time of maximal intubation, Cecal intubation time, landmark identified, quality of bowel prep, etc., can be automatically measured. As these QI metrics can be obtained automatically, it will help to quantify health-care processes and can aid in providing high-quality health care.

Figure 13:
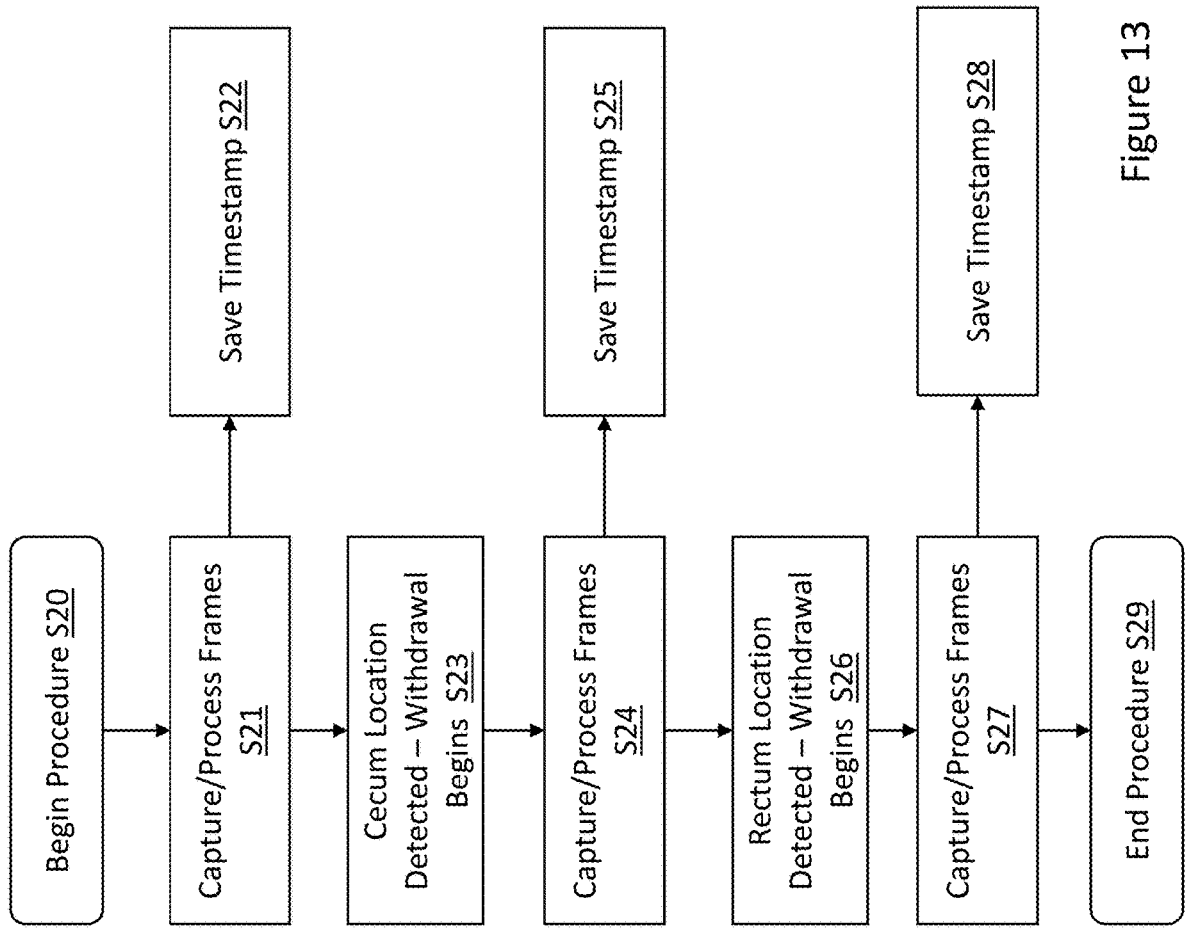
FIG. 13 depicts a process for capturing landmark images and timestamps according to embodiments.

FIG. 13 depicts a flow diagram of an illustrative process of collecting landmarks. In this example, the procedure begins at S20 and a scope (i.e., camera) is inserted. Frames are captured and processed, and a timestamp is recorded at S22. At S23, the cecum location is detected, and withdrawal begins. At S24, frames are captured and processed, and a second timestamp is recorded at S25. Next at S26, the rectum location is detected, and withdrawal begins. At S27, frames are captured and processed, and a third timestamp is recorded at S28. The procedure ends at S29 and the scope is withdrawn.

In this example, a QI for the Total Intubation time for the procedure would be calculated as:

Total Intubation time=Rectum Time (C)−Scope Insert Time (A)

And the Withdrawal Time of the Procedure would be calculated as:

Withdrawal Time=Rectum Time (C)−Cecum Time (B)

Figure 14:
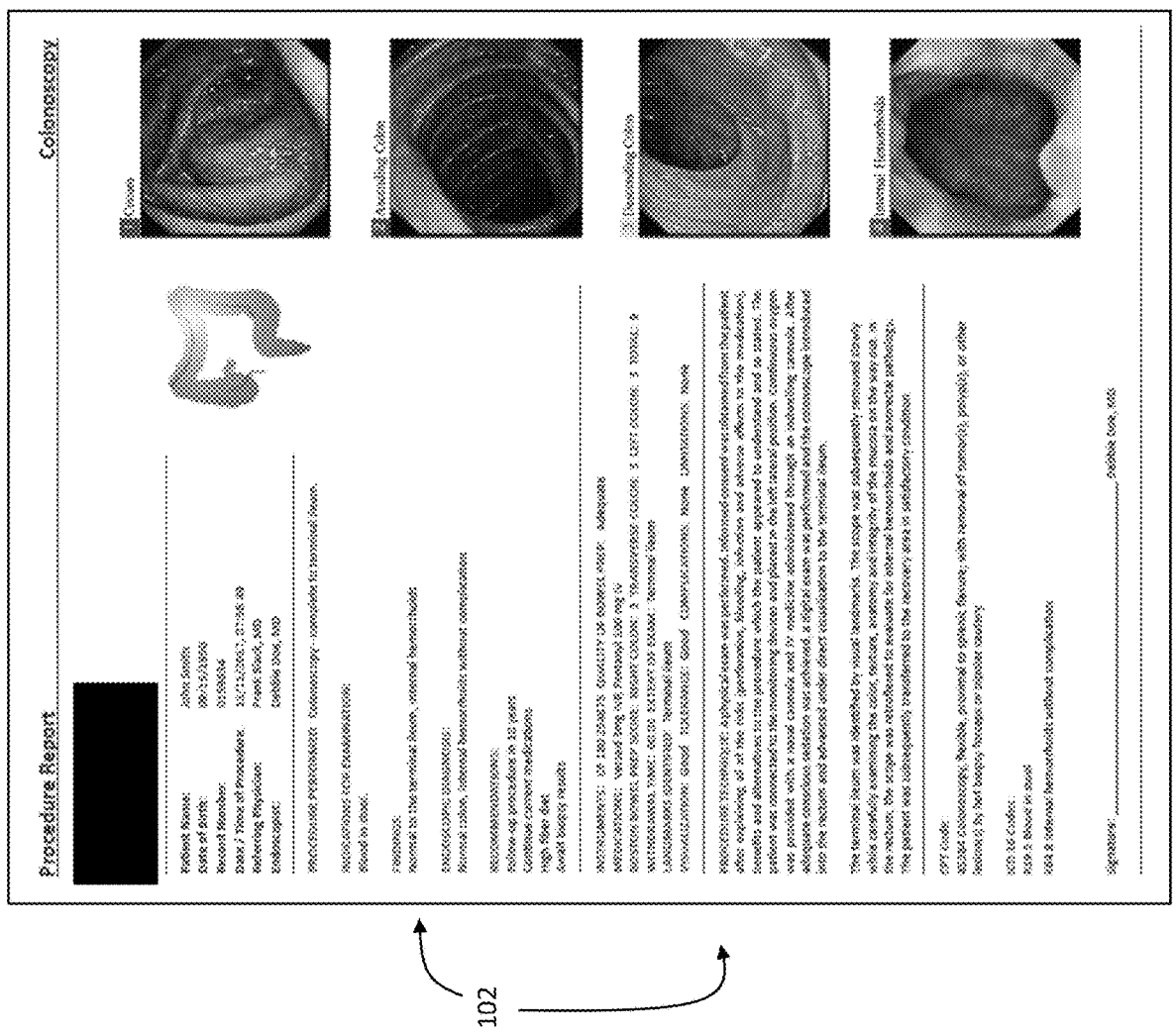
FIGS. 14-15 depict illustrative reports generated by the AI platform according to embodiments.
Figure 15:
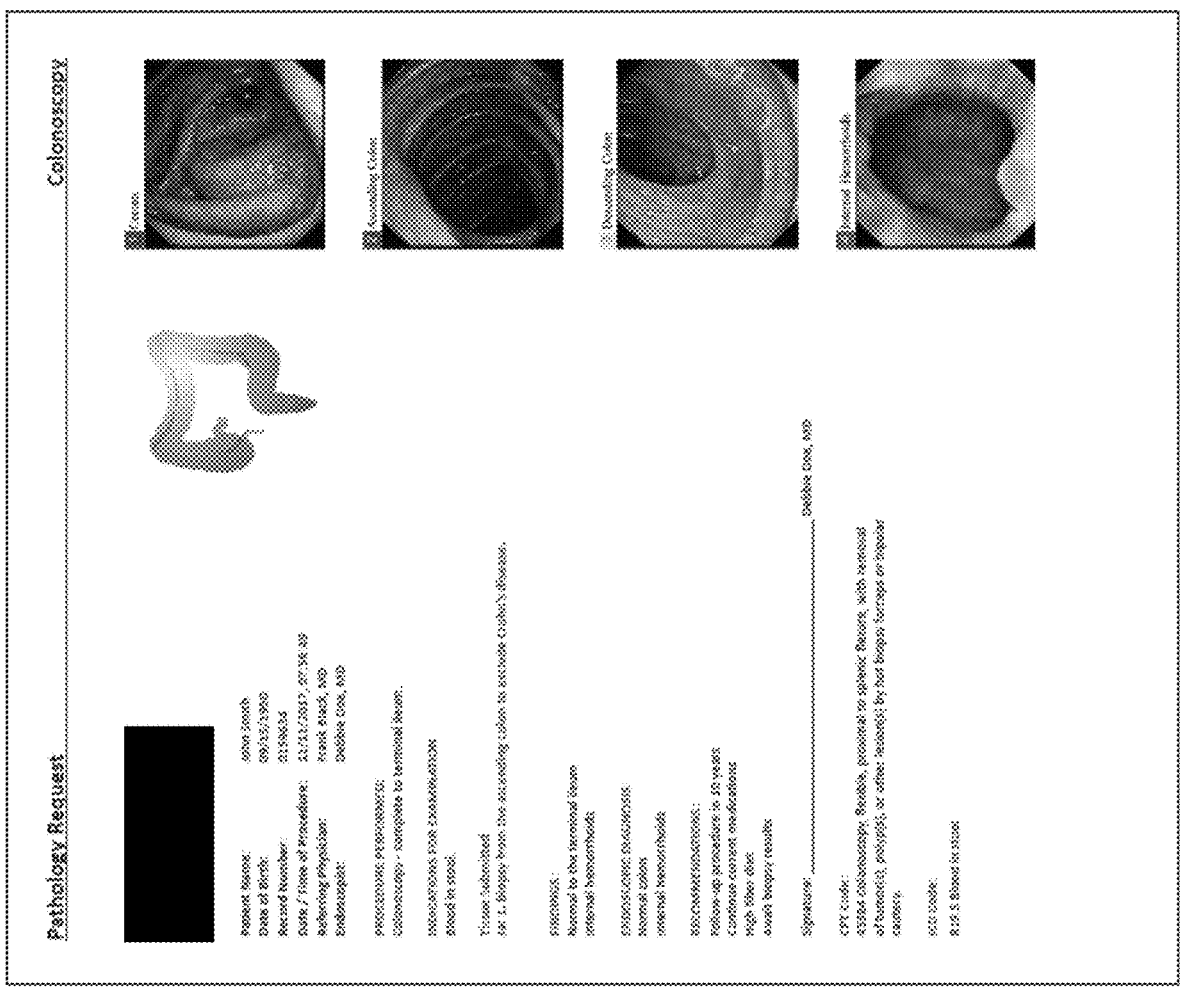

FIGS. 14 and 15 depict illustrative reports that can be automatically generated by the platform. FIG. 14 shows a procedure report 100 that includes landmark images taken during the procedure and structured text sentences 102 arranged in categories, e.g., Indication for Examination, Tissue Submitted, Findings, etc. FIG. 15 depicts a pathology request 104 that likewise includes images taken during the procedure and structured text sentences 106 arranged in categories, e.g., Indication for Examination, Tissue Submitted, Findings, etc. Other reports can similarly be generated with automatically structured sentences including, e.g., letters to physicians, initial consultation forms, follow-up notes, etc.

Figure 16:
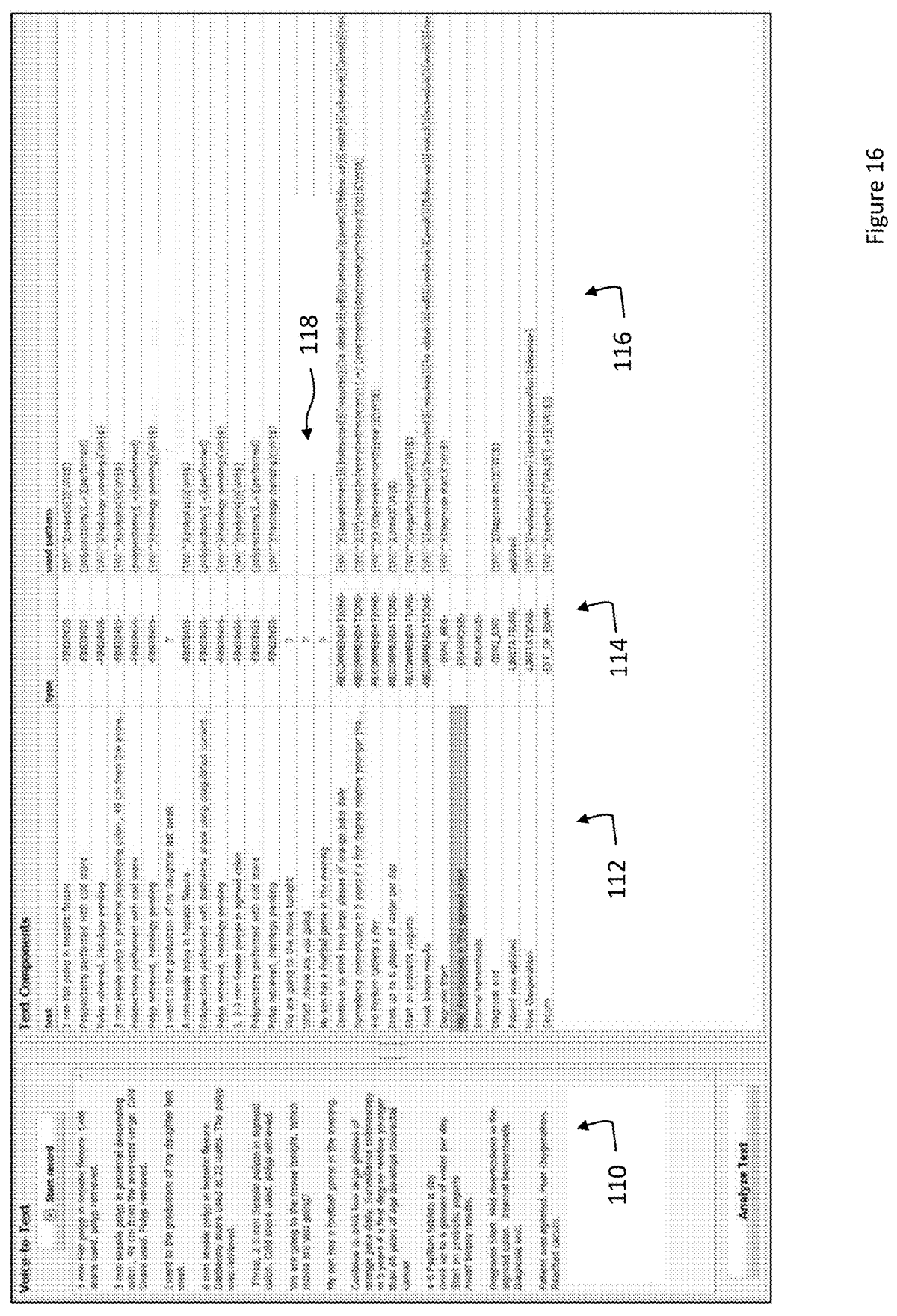

FIG. 16 depicts a summary view of an illustrative user interface. The view includes unstructured text 110 captured during the procedure, structured sentences 112 by the platform, sentence classifications (i.e., types) 114, and regex patterns used 116 to classify each sentence.

Aspects of the disclosure accordingly provide embodiments to recognize patterns in unstructured text by using NLP with Regular Expressions (regex) and deep learning, and image processing using AI to identify QI findings. Classification of data is based on knowledge previously gained or information extracted from patterns and/or their representation. In some embodiments, clinical information is extracted from an unstructured text dataset using a text classifier (NLP) and pattern recognition (regex), after which the user is given an option to use predictive text typing with deep learning to refine the output. Extracted relevant clinical data can be used in clinical report generation, statistical analysis and the discrete data element can be sent to registries. All the unwanted sentences (i.e., noise) in the unstructured text are automatically filtered. In one illustrative embodiment, extracted structured information may include, e.g., Procedure Performed, Extent of Exam, Medications, Findings, Diagnosis, Limitations of Exam, ICD, CPT codes, QIs and data element for registries (e.g., GIQuIC).

During a procedure, two paths collect data. The first path collects speech (i.e., uttered conversation) from the procedure room. The second path collects and classifies live images, e.g., to detect landmarks. In one embodiment involving speech collected from the procedure room, a resulting report is automatically generated. In a second embodiment, speech can be collected during a consultation, and an initial consultation report and progress/follow-up report are automatically generated. In this second embodiment, image data may or may not be included in the reports (i.e., only the first path is utilized).

Figure 17:
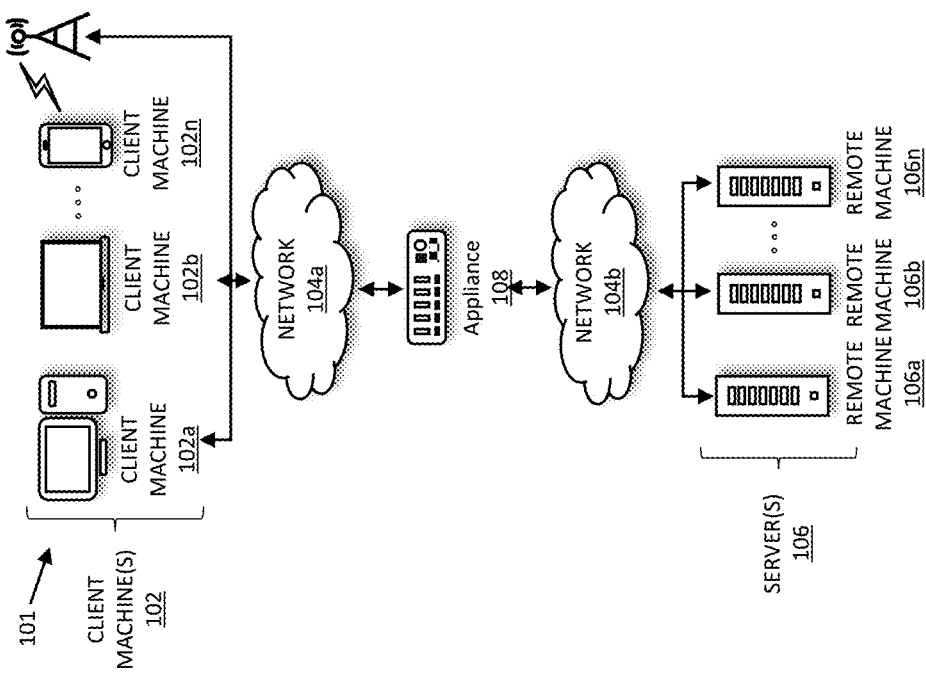
FIG. 17 depicts an illustrative network according to embodiments.

It is understood that the described platform can be implemented using any computing technique, e.g., as a stand-alone system, a distributed system, within a network environment, etc. Referring to FIG. 17, a non-limiting network environment 101 in which various aspects of the disclosure may be implemented includes one or more client machines 102A-102N, one or more remote machines 106A-106N, one or more networks 104, 104', and one or more appliances 108 installed within the computing environment 101. The client machines 102A-102N communicate with the remote machines 106A-106N via the networks 104, 104'.

In some embodiments, the client machines 102A-102N communicate with the remote machines 106A-106N via an intermediary appliance 108. The illustrated appliance 108 is positioned between the networks 104, 104' and may also be referred to as a network interface or gateway. In some embodiments, the appliance 108 may operate as an application delivery controller (ADC) to provide clients with access to business applications and other data deployed in a datacenter, the cloud, or delivered as Software as a Service (SaaS) across a range of client devices, and/or provide other functionality such as load balancing, etc. In some embodiments, multiple appliances 108 may be used, and the appliance(s) 108 may be deployed as part of the network 104 and/or 104'.

The client machines 102A-102N may be generally referred to as client machines 102, local machines 102, clients 102, client nodes 102, client computers 102, client devices 102, computing devices 102, endpoints 102, or endpoint nodes 102. The remote machines 106A-106N may be generally referred to as servers 106 or a server farm 106. In some embodiments, a client device 102 may have the capacity to function as both a client node seeking access to resources provided by a server 106 and as a server 106 providing access to hosted resources for other client devices 102A-102N. The networks 104, 104' may be generally referred to as a network 104. The networks 104 may be configured in any combination of wired and wireless networks.

A server 106 may be any server type such as, for example: a file server; an application server; a web server; a proxy server; an appliance; a network appliance; a gateway; an application gateway; a gateway server; a virtualization server; a deployment server; a Secure Sockets Layer Virtual Private Network (SSL VPN) server; a firewall; a web server; a server executing an active directory; a cloud server; or a server executing an application acceleration program that provides firewall functionality, application functionality, or load balancing functionality.

A server 106 may execute, operate or otherwise provide an application that may be any one of the following: software; a program; executable instructions; a virtual machine; a hypervisor; a web browser; a web-based client; a client-server application; a thin-client computing client; an ActiveX control; a Java applet; software related to voice over internet protocol (VoIP) communications like a soft IP telephone; an application for streaming video and/or audio; an application for facilitating real-time-data communications; a HTTP client; a FTP client; an Oscar client; a Telnet client; or any other set of executable instructions.

In some embodiments, a server 106 may execute a remote presentation services program or other program that uses a thin-client or a remote-display protocol to capture display output generated by an application executing on a server 106 and transmit the application display output to a client device 102.

In yet other embodiments, a server 106 may execute a virtual machine providing, to a user of a client device 102, access to a computing environment. The client device 102 may be a virtual machine. The virtual machine may be managed by, for example, a hypervisor, a virtual machine manager (VMM), or any other hardware virtualization technique within the server 106.

In some embodiments, the network 104 may be: a local-area network (LAN); a metropolitan area network (MAN); a wide area network (WAN); a primary public network 104; and a primary private network 104. Additional embodiments may include a network 104 of mobile telephone networks that use various protocols to communicate among mobile devices. For short range communications within a wireless local-area network (WLAN), the protocols may include 802.11, Bluetooth, and Near Field Communication (NFC).

Figure 18:
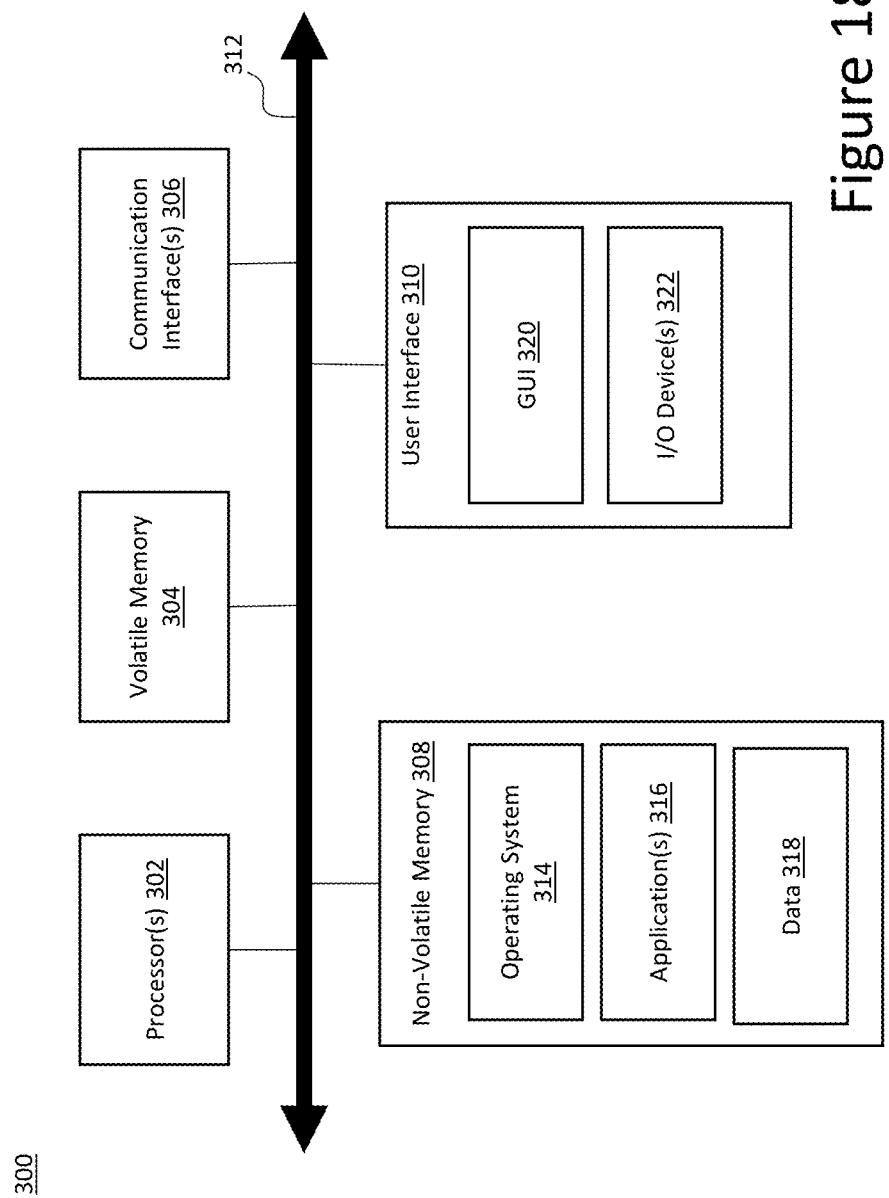
FIG. 18 depicts an illustrative computing system according to embodiments.

Elements of the described solution may be embodied in a computing system, such as that shown in FIG. 18 in which a computing device 300 may include one or more processors 302, volatile memory 304 (e.g., RAM), non-volatile memory 308 (e.g., one or more hard disk drives (HDDs) or other magnetic or optical storage media, one or more solid state drives (SSDs) such as a flash drive or other solid state storage media, one or more hybrid magnetic and solid state drives, and/or one or more virtual storage volumes, such as a cloud storage, or a combination of such physical storage volumes and virtual storage volumes or arrays thereof), user interface (UI) 310, one or more communications interfaces 306, and communication bus 312. User interface 310 may include graphical user interface (GUI) 320 (e.g., a touch-screen, a display, etc.) and one or more input/output (I/O) devices 322 (e.g., a mouse, a keyboard, etc.). Non-volatile memory 308 stores operating system 314, one or more applications 316, and data 318 such that, for example, computer instructions of operating system 314 and/or applications 316 are executed by processor(s) 302 out of volatile memory 304. Data may be entered using an input device of GUI 320 or received from I/O device(s) 322. Various elements of computer 300 may communicate via communication bus 312. Computer 300 as shown in FIG. 6 is shown merely as an example, as clients, servers and/or appliances and may be implemented by any computing or processing environment and with any type of machine or set of machines that may have suitable hardware and/or software capable of operating as described herein.

Processor(s) 302 may be implemented by one or more programmable processors executing one or more computer programs to perform the functions of the system. As used herein, the term "processor" describes an electronic circuit that performs a function, an operation, or a sequence of operations. The function, operation, or sequence of operations may be hard coded into the electronic circuit or soft coded by way of instructions held in a memory device. A "processor" may perform the function, operation, or sequence of operations using digital values or using analog signals. In some embodiments, the "processor" can be embodied in one or more application specific integrated circuits (ASICs), microprocessors, digital signal processors, microcontrollers, field programmable gate arrays (FPGAs), programmable logic arrays (PLAs), multi-core processors, or general-purpose computers with associated memory. The "processor" may be analog, digital or mixed-signal. In some embodiments, the "processor" may be one or more physical processors or one or more "virtual" (e.g., remotely located or "cloud") processors.

Communications interfaces 306 may include one or more interfaces to enable computer 300 to access a computer network such as a LAN, a WAN, or the Internet through a variety of wired and/or wireless or cellular connections.

In described embodiments, a first computing device 300 may execute an application on behalf of a user of a client computing device (e.g., a client), may execute a virtual machine, which provides an execution session within which applications execute on behalf of a user or a client computing device (e.g., a client), such as a hosted desktop session, may execute a terminal services session to provide a hosted desktop environment, or may provide access to a computing environment including one or more of: one or more applications, one or more desktop applications, and one or more desktop sessions in which one or more applications may execute.

As will be appreciated by one of skill in the art upon reading the following disclosure, various aspects described herein may be embodied as a system, a device, a method or a computer program product (e.g., a non-transitory computer-readable medium having computer executable instruction for performing the noted operations or steps). Accordingly, those aspects may take the form of an entirely hardware embodiment, an entirely software embodiment, or an embodiment combining software and hardware aspects. Furthermore, such aspects may take the form of a computer program product stored by one or more computer-readable storage media having computer-readable program code, or instructions, embodied in or on the storage media. Any suitable computer readable storage media may be utilized, including hard disks, CD-ROMs, optical storage devices, magnetic storage devices, and/or any combination thereof.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The foregoing drawings show some of the processing associated according to several embodiments of this disclosure. In this regard, each drawing or block within a flow diagram of the drawings represents a process associated with embodiments of the method described. It should also be noted that in some alternative implementations, the acts noted in the drawings or blocks may occur out of the order noted in the figure or, for example, may in fact be executed substantially concurrently or in the reverse order, depending upon the act involved. Also, one of ordinary skill in the art will recognize that additional blocks that describe the processing may be added.

What is claimed is:

1. An artificial intelligence (AI) platform for processing information collected during a medical procedure, comprising:
   an image processing system that processes images captured with a scope during the procedure using an image classifier to identify image-based quality-of-care indicators (QIs), wherein training of the image classifier includes analyzing pictures of landmarks obtained from prior clinical procedures, and wherein at least one of the QIs includes one of a total intubation time or a withdrawal time of the scope calculated with time stamps recorded in response to the image classifier recognizing predefined landmarks in the captured images;
   a system for collecting unstructured natural language (NL) uttered during the procedure, wherein the unstructured NL includes informal medical expressions;
   a natural language (NL) processing system that processes the unstructured NL and includes:
      creating sentences from the unstructured NL;
      performing a search and replace to locate informal medical expressions in the sentences and to replace informal medical expressions with standardized expressions from a medical dictionary, wherein the informal medical expressions are located using predefined text patterns determined with an automated learning process;
      identifying text-based QIs in the sentences;
      classifying sentences into sentence types based on a trained model; and
      updating sentences by integrating the image-based QIs with text-based QIs;
   an editor for displaying and editing sentences, wherein the editor includes a next word prediction system that utilizes a predictive model, wherein the predictive model trained by:
      inputting a training set including word groups,
      analyzing each word group to identify a next possible word and probability of the next possible word's appearance, and
      building a word hierarchy based on frequency of word usage in the training set; and
   an output module configured to output structured data that includes sentences organized by sentence type and images organized by image-based QIs.

2. The AI platform of claim 1:
   wherein the procedure includes at least one of: a colonoscopy procedure, a gastronomy procedure or a clinical procedure; and
   wherein the image-based QIs include landmarks involving at least one of: a lesion, a cecum, a rectum, an ascending colon, a descending colon, and a hemorrhoid.

3. The AI platform of claim 2, wherein the image-based QIs further include at least one of: polyps detected, polyp size, and histology.

4. The AI platform of claim 1, wherein performing a search and replace on predefined text patterns includes using regular expressions (regex) to identify patterns.

5. The AI platform of claim 4, wherein identified patterns are replaced with standardized medical expressions.

6. The AI platform of claim 1, wherein the NL processing system further includes filtering out irrelevant sentences.

7. The AI platform of claim 1, wherein the next word prediction system uses a Markov Chain Algorithm.

8. The AI platform of claim 1, wherein the output module is configurable to output a medical report, an Electronic Medical Record (EMR), and a QI registry entry.

9. The AI platform of claim 1, wherein the output module is configurable to output a medical report with sections organized by sentence type.

10. A method for processing information collected during a medical procedure, comprising:
    capturing images and unstructured natural language (NL) during a medical procedure, wherein the unstructured NL includes informal medical expressions;
    processing the images using an image classifier to identify image-based quality-of-care indicators (QIs) including procedure time metrics, wherein training of the image classifier includes analyzing pictures of landmarks obtained from prior clinical procedures;
    creating sentences from the unstructured NL;
    performing a search and replace to locate informal medical expressions and to replace informal medical expressions with standardized expressions from a medical dictionary, wherein the informal medical expressions are located using predefined text patterns determined with an automated learning process;
    identifying text-based QIs in the sentences;
    classifying sentences into sentence types using a trained model, the trained model trained by:
       inputting a training set including word groups,
       analyzing each word group to identify a next possible word and probability of the next possible word's appearance, and
       building a word hierarchy based on frequency of word usage in the training set,
    updating sentences by integrating the image-based QIs with text-based QIs; and
    outputting structured data that includes sentences organized by sentence type.

11. The method of claim 10, wherein the procedure includes a colonoscopy and the image-based QIs include landmarks involving at least one of: a cecum, a rectum, an ascending colon, a descending colon, and a hemorrhoid.

12. The method of claim 11, wherein the image-based QIs further include at least one of: landmarks, polyps detected, polyp size, and histology.

13. The method of claim 10, wherein performing a search and replace on predefined text patterns includes using regular expressions (regex) to identify patterns.

14. The method of claim 13, wherein identified patterns are replaced with standardized medical expressions.

15. The method of claim 10, further comprising providing an editor for displaying and editing sentences, wherein the editor includes a next word prediction system.

16. The method of claim 15, wherein the next word prediction system uses a Markov Chain Algorithm wherein the training set is a database of medical records.

17. The method of claim 10, wherein the structured data includes at least one of a medical report, an Electronic Medical Record (EMR), and a QI registry entry.

18. The method of claim 10, wherein the output module is configurable to output a medical report with sections organized by sentence type.

19. A system, comprising:
    a camera for collecting image data during a medical procedure;
    a microphone for collecting speech during the medical procedure;

an image processing system that processes image data using an image classifier to identify image-based quality-of-care indicators (QIs);

a natural language (NL) processing system that processes unstructured NL captured from speech uttered during the procedure and is configured to:
  create sentences from the unstructured NL;
  perform a search and replace to locate informal medical expressions in the sentences and to replace informal medical expressions with standardized expressions from a medical dictionary, wherein the informal medical expressions are located using predefined text patterns determined with an automated learning process;
  identify text-based QIs in the sentences;
  classify sentences into sentence types based on a trained model; and
  update sentences by integrating the image-based QIs with text-based QIs;

an editor for displaying and editing sentences, wherein the editor includes a next word prediction system that utilizes a predictive model, wherein training of the predictive model includes:
  inputting a training set including word groups,
  analyzing each word group to identify a next possible word and probability of the next possible word's appearance, and
  building a word hierarchy based on frequency of word usage in the training set, and an output module configured to output structured data that includes sentences organized by sentence type and images organized by image-based QIs.

* * * * *